(12) United States Patent
Maekawa (10) Patent No.: US 9,577,462 B2
(45) Date of Patent: Feb. 21, 2017

(54) POWER TRANSMISSION SYSTEM

(71) Applicant: IHI Corporation, Tokyo (JP)

(72) Inventor: Yuji Maekawa, Tokyo (JP)

(73) Assignee: IHI CORPORATION (JP)

( * ) Notice: Subject to any disclaimer, the term of this patent is extended or adjusted under 35 U.S.C. 154(b) by 485 days.

(21) Appl. No.: 14/266,911

(22) Filed: May 1, 2014

(65) Prior Publication Data

US 2014/0232200 A1 Aug. 21, 2014

Related U.S. Application Data

(63) Continuation of application No. PCT/JP2012/081781, filed on Dec. 7, 2012.

(30) Foreign Application Priority Data

Dec. 7, 2011 (JP) .................. 2011-268250

(51) Int. Cl.
| | | |
|---|---|---|
| *H02J 7/02* | (2016.01) | |
| *B63G 8/00* | (2006.01) | |
| *H02J 5/00* | (2016.01) | |
| *B63G 8/08* | (2006.01) | |
| *G01N 33/18* | (2006.01) | |

(52) U.S. Cl.
CPC .............. *H02J 7/025* (2013.01); *B63G 8/001* (2013.01); *B63G 8/08* (2013.01); *G01N 33/1886* (2013.01); *H02J 5/005* (2013.01); *B63B 2211/02* (2013.01); *B63G 2008/008* (2013.01)

(58) Field of Classification Search
CPC ........ H02J 5/005; H02J 7/025; G01N 33/1886
See application file for complete search history.

(56) References Cited

U.S. PATENT DOCUMENTS

| | | | |
|---|---|---|---|
| 8,304,935 B2 | 11/2012 | Karalis et al. ................. | 307/104 |
| 2010/0007214 A1* | 1/2010 | Howard ................ | B60L 11/182 |
| | | | 307/104 |
| 2011/0043047 A1 | 2/2011 | Karalis ......................... | 307/104 |

(Continued)

FOREIGN PATENT DOCUMENTS

| | | |
|---|---|---|
| CN | 1800871 A | 7/2006 |
| CN | 1802123 A | 7/2006 |

(Continued)

OTHER PUBLICATIONS

European Search Report, dated Jul. 21, 2015, issued in corresponding European Patent Application No. 12856483.8. Total 4 pages.

(Continued)

*Primary Examiner* — Jeffrey Shin
(74) *Attorney, Agent, or Firm* — Ostrolenk Faber LLP (57) ABSTRACT

A power transmission system transmits power underwater between a power-transmitting device and a power-receiving device of which at least one is capable of moving freely underwater. In this power transmission system, the power-transmitting device and the power-receiving device are each provided with a resonance coil that performs the power transmission wirelessly underwater by means of magnetic field resonance. At least one of the power-transmitting device and the power-receiving device is provided with a balloon that internally houses the resonance coil of its own device.

6 Claims, 5 Drawing Sheets

(56) References Cited

U.S. PATENT DOCUMENTS

2013/0321223 A1* 12/2013 Bokenfohr ............... H01Q 1/04
343/719

FOREIGN PATENT DOCUMENTS

| CN | 102214955 A | 10/2011 |
|---|---|---|
| CN | 102265479 A | 11/2011 |
| JP | 62-122435 | 8/1987 |
| JP | 02-032721 | 2/1990 |
| JP | 3493426 | 2/2004 |
| JP | 2004-166459 | 6/2004 |
| JP | 2011-239671 | 11/2011 |

OTHER PUBLICATIONS

Ze-Song Li, et al., "Design Considerations for Electromagnetic Couplers in Contactless Power Transmission Systems for Deep-Sea Applications" *Journal of Zhejiang University Science C. (Computers & Electronics)* Zhejiang University Press. China. vol. 11, No. 10 (Oct. 2010) XP-002741738. ISSN:1869-1951. pp. 824-834.

Tim McGinnis, et al., "Inductive Power System for Autonomous Underwater Vehicles" *Oceans 2007, IEEE*, Piscataway, NJ (Sep. 2007) pp. 1-5.

Tomohiro Kojiya, et al., "Automatic Power Supply System to Underwater Vehicles Utilizing Non-Contacting Technology" *Oceans '04. MTTS/IEEE Techno-Ocean '04* Kobe, Japan Nov. 9-12; (Nov. 2004) Piscataway, NJ. vol. 4. pp. 2341-2345.

Office Action dated Sep. 25, 2015 in corresponding Chinese Patent Application No. 201280059930.3 with English language translation (18 pages).

International Search Report and Written Opinion mailed Feb. 19, 2013 in corresponding PCT International Application No. PCT/JP2012/081781.

Japanese Office Action, dated Jul. 1, 2014, issued in corresponding Japanese Patent Application No. 2013-548313. English translation. Total 3 pages.

* cited by examiner

POWER TRANSMISSION SYSTEM

This application is a continuation application based on a PCT Patent Application No. PCT/JP2012/081781, filed Dec. 7, 2012, whose priority is claimed on Japanese Patent Application No. 2011-268250, filed Dec. 7, 2011. The contents of both the PCT application and the Japanese Patent Application are incorporated herein by reference.

TECHNICAL FIELD

The present invention relates to a power transmission system.

BACKGROUND ART

Conventionally, a method of examining the water quality of sea water using an autonomous underwater vehicle that travels through water by means of battery power is known. Naturally, if the residual battery power of the autonomous underwater vehicle drops to zero, it becomes impossible to collect data relating to the water quality or to travel through the water. Because of this, when the residual battery power drops below a specified value, it is normal for the autonomous underwater vehicle to be recovered to a surface vessel so that the battery can be charged.

In this manner, if the autonomous underwater vehicle is recovered to the surface vessel each time the battery needs charging, then both the time required and the costs increase enormously. As a consequence, in recent years, advances have been made in the development of technology to enable this charging to be performed underwater. For example, in Patent document 1 (see below), technology is disclosed in which a battery that is installed in an underwater station that collects data relating to the water quality of sea water is charged by an underwater robot that travels through the water using a wireless power supply system (in particular, an electromagnetic induction system).

DOCUMENT OF RELATED ART

Patent Documents

[Patent document 1] Japanese Patent Application Laid-Open (JP-A) No. 2004-166459
[Patent document 2] Japanese Patent No. 3493426
[Patent document 3] U.S. Pat. No. 8,304,935

SUMMARY OF INVENTION

Technical Problem

As in the aforementioned conventional technology, when an electromagnetic induction system is used as the wireless power supply system, in order to maximize the power transmission efficiency, it is necessary to accurately position the power-transmitting device (i.e., the underwater robot) and the power-receiving device (i.e., the underwater station) during the underwater power transmission (i.e., during the battery charging). Accordingly, it has been necessary to install a high-accuracy positioning mechanism for this purpose, so that the problem of high system costs has arisen.

The present invention was conceived in view of the above-described circumstances and it is an object thereof to provide a power transmission system that makes it possible to achieve underwater power transmissions at low cost between a power-transmitting device and a power-receiving device of which at least one is capable of moving freely underwater.

Solution to Problem

In order to achieve the above-described object, according to a first aspect of the present invention, in a power transmission system that transmits power underwater between a power-transmitting device and a power-receiving device of which at least one is capable of moving freely underwater, the power-transmitting device and the power-receiving device are each provided with a resonance coil that performs the power transmission wirelessly underwater by means of magnetic field resonance. At least one of the power-transmitting device and the power-receiving device is provided with a balloon that internally houses the resonance coil of its host device.

Moreover, according to a second aspect of the present invention, in the above-described first aspect at least one of the power-transmitting device and the power-receiving device is provided with a balloon control mechanism that, during a power transmission, causes the balloon to inflate, and at other times, causes the balloon to be deflated.

Moreover, according to a third aspect of the present invention, in the above-described first or second aspects the power-receiving device is an autonomous underwater vehicle that collects water quality data as it moves through the water under battery power. The power-transmitting device is an underwater base station that is installed in a predetermined location underwater and is connected by a cable to an on-land electrical power system, and receives from the electrical power system a supply of power that is to be transmitted to the autonomous underwater vehicle.

Moreover, according to a fourth aspect of the present invention, in the above-described third aspect the autonomous underwater vehicle wirelessly transmits the water quality data to the underwater base station during a power transmission. The underwater base station is connected by cable to an on-land water quality data control device, and transmits the water quality data that it receives from the autonomous underwater vehicle by cable to the water quality data control device.

Effects of the Invention

In the present invention, a magnetic field resonance system is employed for underwater power transmissions between a power-transmitting device and a power-receiving device. Compared to an electromagnetic induction system, this magnetic field resonance system is largely unaffected by positional shifting of the resonance coils that are provided in both the power-transmitting device and the power-receiving device (i.e., is tolerant of positional shift), and is able to perform power transmissions highly efficiently and over long distances using only a weak magnetic field.

Accordingly, according to the present invention, a high-accuracy positioning mechanism such as is used in the conventional technology which employs an electromagnetic induction system is rendered unnecessary. As a consequence, it is possible to achieve underwater power transmissions at low cost between a power-transmitting device and a power-receiving device. Moreover, in the present invention, at least one of the resonance coils of the power-transmitting device and the power-receiving device is covered by a balloon. As a result, it is possible to prevent the magnetic field being disrupted by the effects of ions and the like contained in the water, and to thereby prevent the power transmission efficiency between the power-transmitting device and the power-receiving device from deteriorating.

DESCRIPTION OF EMBODIMENTS

Hereinafter, an embodiment of the present invention will be described with reference made to the drawings.

Figure 1:
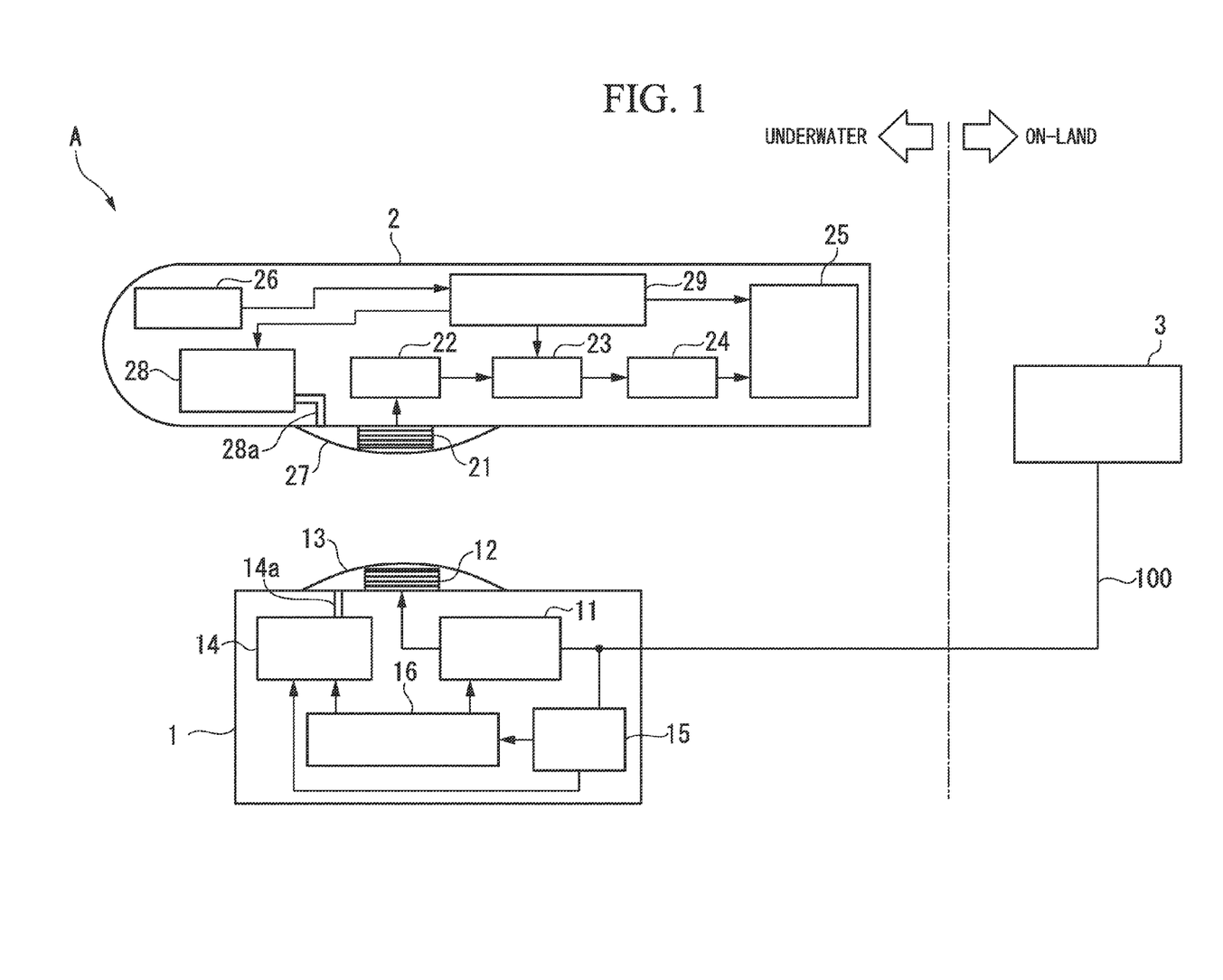
FIG. 1 is a schematic structural view of a power transmission system according to the present embodiment.

FIG. 1 is a schematic structural view of a power transmission system A according to the present embodiment. As is shown in FIG. 1, the power transmission system A is provided with an underwater base station 1 (i.e., a power-transmitting device) that is installed in a predetermined underwater location, and an autonomous underwater vehicle 2 (i.e., a power-receiving device) that is able to move freely underwater by means of battery power, and with an electrical power system 3 that is installed on land.

The underwater base station 1 is connected via a power supply cable 100 to the on-land electrical power system 3, and wirelessly transmits (i.e., supplies) AC power (for example, 100 V single-phase power having a frequency of 50 or 60 Hz) that is supplied from the electrical power system 3 to the autonomous underwater vehicle 2 by means of magnetic field resonance. The underwater base station 1 is provided with an AC/AC converter 11, a power transmission resonance coil 12, a power transmission balloon 13, a power transmission balloon control mechanism 14, a power supply circuit 15, and a base station control device 16.

Under the control of the base station control device 16, the AC/AC converter 11 converts AC power that is supplied via the power supply cable 100 from the on-land electrical power system 3 into AC power that has a predetermined voltage and a predetermined frequency that are suitable for a power transmission via magnetic field resonance. The AC/AC converter 11 outputs the converted AC power to the power transmission resonance coil 12.

The power transmission resonance coil 12 is a spirally-wound helical coil that is used to transmit the AC power input from the AC/AC converter 11 wirelessly by means of magnetic field resonance. The power transmission resonance coil 12 is installed such that it protrudes above the underwater base station 1. An LC resonance circuit is formed by the power transmission resonance coil 12 and by a capacitor (not shown). Note that it is possible to use the parasitic capacity of the helical coil as the capacitor that is used to form the LC resonant circuit, or alternatively, it is also possible to provide a separate capacitor element. Moreover, it is also possible to provide a core that is formed from a material having high magnetic permeability such as ferrite inside the coil portion of the helical coil.

The power transmission balloon 13 is provided on an external wall surface of the underwater base station 1 so as to house inside itself the power transmission resonance coil 12. The power transmission balloon 13 is able to inflate and deflate freely. It is desirable for the power transmission balloon 13 to be formed from a resin (and particularly from rubber) such that it does not affect the magnetic field generated between the power transmission resonance coil 12 and the power reception resonance coil 21. It is particularly desirable for the balloon component that is placed between the coils to be formed from graphite rubber, which has a high magnetic permeability, and it is desirable for the balloon component on the side that is not located between the coils to be formed from rubber that contains foil, powder or particles of a paramagnetic substance such as aluminum or copper that has a low magnetic permeability.

Note that in FIG. 1, a state is shown in which the power transmission balloon 13 is deflated.

Under the control of the base station control unit 16, the power transmission balloon control mechanism 14 inflates the power transmission balloon 13 during a power transmission, and deflates the power transmission balloon 13 during other times (i.e., times when power is not being transmitted). Specifically, the power transmission balloon control mechanism 14 causes the power transmission balloon 13 to be inflated by feeding gas to the interior of the power transmission balloon 13 via a gas tube 14a. In contrast, the power transmission balloon control mechanism 14 causes the power transmission balloon 13 to be deflated by suctioning gas from the interior of the power transmission balloon 13 via the gas tube 14a.

In order to make the supply and removal of this gas more efficient, it is preferable for a plurality of the gas tubes 14a to be provided.

By providing a partition inside the balloons so as to form a plurality of chambers, and then connecting a gas tube 14a to each one of these chambers, and then supplying or removing the gas to the individual chambers via the power transmission balloon control mechanism 14, it is possible to adjust the position and angle between the coils, and to also thereby control the position and angle between the coils relative to each other.

It is desirable for side surfaces of the balloons to be structured in the form of a bellows such that, when gas is being supplied to the interior of a balloon, the balloon inflates so as to fill the space between the power transmission coil and the power reception coil, but with only a small amount of inflation in the side surface direction of each coil.

It is desirable for an inert gas such as nitrogen to be used for the gas, however, dry air may also be used.

Moreover, instead of using gas, it is also possible to use a non-corrosive organic material in liquid form, or water with a low content of ions or impurities (for example, water from which impurities have been removed by an ion-exchange resin).

The power supply circuit 15 uses AC power that is supplied via the power supply cable 100 from the on-land electrical power system 3, and generates power supply voltage for use inside the underwater base station 1. The power supply circuit 15 outputs the generated power supply voltage to the base station control unit 16 and the power transmission balloon control mechanism 14. The base station control unit 16 is provided with a microprocessor and memory and the like, and, in accordance with control programs that have been stored in advance in its memory, controls the AC/AC converter 11 and the power transmission balloon control mechanism 14 during the transmission of power to the autonomous underwater vehicle 2.

The autonomous underwater vehicle 2 collects data relating to water quality (hereinafter, this is expressed as 'water quality data') while traveling through the water by battery power, and when its battery is being recharged, receives AC power from the underwater base station 1 by means of magnetic field resonance. The autonomous underwater vehicle 2 is provided with a power reception resonance coil 21, a rectifier circuit 22, a charging circuit 23, a battery 24, a propulsion/steering mechanism 25, a water quality sensor 26, a power reception balloon 27, a power reception balloon control mechanism 28, and an autonomous vehicle control unit 29.

The power reception resonance coil 21 is a spirally-wound helical coil that is used to receive AC power input from the power transmission resonance coil 12 of the underwater base station 1 wirelessly. The power reception resonance coil 21 is installed such that it protrudes below the autonomous underwater vehicle 2. An LC resonance circuit is formed by the power reception resonance coil 21 and by a capacitor (not shown). If the circuit constants of the LC resonance circuits of both the underwater base station 1 and the autonomous underwater vehicle 2 are set such that these resonance circuits are mutually equal, then it becomes possible to make magnetic field resonance occur between the power transmission resonance coil 12 and the power reception resonance coil 21.

The rectifier circuit 22 rectifies the AC power received by the power reception resonance coil 21 so as to convert it into DC power, and then outputs this DC power to the charging circuit 23. Under the control of the autonomous vehicle control unit 29, the charging circuit 23 uses the DC power input by the rectifier circuit 22 to output to the battery 24 suitable voltage and current for charging the battery 24.

The battery 24 is used as an internal power source by the autonomous underwater vehicle 2 and is a secondary cell such as, for example, a nickel hydrogen cell or a lithium ion cell, and outputs a power supply voltage (i.e., DC voltage) to the propulsion/steering mechanism 25. Note that, although omitted from FIG. 1, the battery 24 also supplies a power supply voltage to the water quality sensor 26, the power reception balloon control mechanism 28, and the autonomous vehicle control unit 29. Moreover, when necessary, it is also possible to provide a DC/DC converter that converts the output voltage from the battery 24 to a desired value.

The propulsion/steering mechanism 25 consists of a propeller and rudder, and of a drive mechanism (including a motor and motor driver and the like) that is used to drive these. Under the control of the autonomous vehicle control unit 29, the propulsion/steering mechanism 25 generates the propulsion force of the autonomous underwater vehicle 1 and also regulates the direction of travel thereof. The water quality sensor 26 detects the quality of seawater (for example, the water temperature, transparency, pH, nitrogen concentration, phosphorus concentration, and the like), and outputs these detection results as water quality data to the autonomous vehicle control unit 29.

The power reception balloon 27 is provided on an external wall surface of the autonomous underwater vehicle 2 so as to house inside itself the power reception resonance coil 21. The power reception balloon 27 is able to inflate and deflate freely. It is desirable for the power reception balloon 27 to be formed from a resin (and particularly from rubber) such that it does not affect the magnetic field generated between the power transmission resonance coil 12 and the power reception resonance coil 21. Note that in FIG. 1, a state is shown in which the power reception balloon 27 is completely deflated. It is particularly desirable for components that are located between the coils to be formed from graphite rubber, which has a high magnetic permeability, and it is desirable for components on the side that are not located between the coils to be formed from rubber that contains foil, powder or particles of a paramagnetic substance such as aluminum or copper that has a low magnetic permeability.

Under the control of the autonomous vehicle control unit 29, the power reception balloon control mechanism 28 inflates the power reception balloon 27 during a power transmission, and deflates the power reception balloon 27 during other times (i.e., times when power is not being transmitted). Specifically, the power reception balloon control mechanism 28 causes the power reception balloon 27 to be inflated by feeding gas to the interior of the power reception balloon 27 via a gas tube 28a. In contrast, the power reception balloon control mechanism 28 causes the power reception balloon 27 to be deflated by suctioning gas from the interior of the power reception balloon 27 via the gas tube 28a.

It is desirable for side surfaces of the balloons to be structured in the form of a bellows such that, when gas is being supplied to the interior of a balloon, the balloon inflates so as to fill the space between the power transmission coil and the power reception coil, but with only a small amount of inflation in the side surface direction of each coil.

The autonomous vehicle control unit 29 is provided with a microprocessor and memory and the like, and, in accordance with control programs that have been stored in advance in its memory, controls the propulsion/steering mechanism 25 and collects water quality data from the water quality sensor 26 (i.e., stores this water quality data in its memory). When the battery 24 is being charged (i.e., when power is being transmitted from the underwater base station 1 to the autonomous underwater vehicle 2), the autonomous vehicle control unit 29 controls the charging circuit 23 and the power reception balloon control mechanism 28.

Next, operations of the power transmission system A according to the first embodiment that has the above-described structure will be described in detail.

Firstly, a normal mode operation will be described. The autonomous vehicle control unit 29 of the autonomous underwater vehicle 2 controls the propulsion/steering mechanism 25 such that the autonomous underwater vehicle 2 travels through the water following a prescribed route. As a result of this, the autonomous underwater vehicle 2 travels through the water following a prescribed route. During this time, the autonomous vehicle control unit 29 acquires water quality data at a fixed time interval from the water quality sensor 26, and sequentially stores this acquired water quality data in its memory.

In the above-described normal mode, if the power-reception balloon 27 of the autonomous underwater vehicle 2 is inflated, it obstructs the movement through the water of the autonomous underwater vehicle 2. However, the autonomous vehicle control unit 29 controls the power reception balloon control mechanism 28 such that the power reception balloon 27 is completely deflated. In this normal mode, it is not necessary for power to be transmitted from the underwater base station 1 to the autonomous underwater vehicle 2. Because of this, the base station control unit 16 of the underwater base station 1 stops the control of the AC/AC converter 11, and also controls the power transmission balloon control mechanism 14 such that the power transmission balloon 13 is completely deflated.

When the autonomous vehicle control unit 29 of the autonomous underwater vehicle 2 detects that the residual power of the battery 24 in the above-described normal mode has dropped below a specified value, it switches to charging mode in order to charge the battery 24. When the autonomous vehicle control unit 29 switches to charging mode, it controls the propulsion/steering mechanism 25 such that the autonomous underwater vehicle 2 is made to move to a position above the underwater base station 1. Note that the underwater base station 1 is located on the travel route of the autonomous underwater vehicle 2. The autonomous vehicle control unit 29 ascertains the position where the underwater base station 1 is installed from outputs from a position sensor (not shown) such as a sound wave sensor or optical sensor or the like.

When the autonomous vehicle control unit 29 of the autonomous underwater vehicle 2 has detected from the output from the position sensor in the form of a sound wave sensor or optical sensor or the like that the autonomous underwater vehicle 2 has moved to a position above the underwater base station 1, it controls the power reception balloon control mechanism 28 such that the power reception balloon 27 is completely inflated. Meanwhile, when the base station control unit 16 of the underwater base station 1 has detected from the output from the position sensor in the form of a sound wave sensor or optical sensor or the like that the autonomous underwater vehicle 2 has moved to a position above the underwater base station 1, it controls the power transmission balloon control mechanism 14 such that the power transmission balloon 13 is completely inflated.

Figure 2:
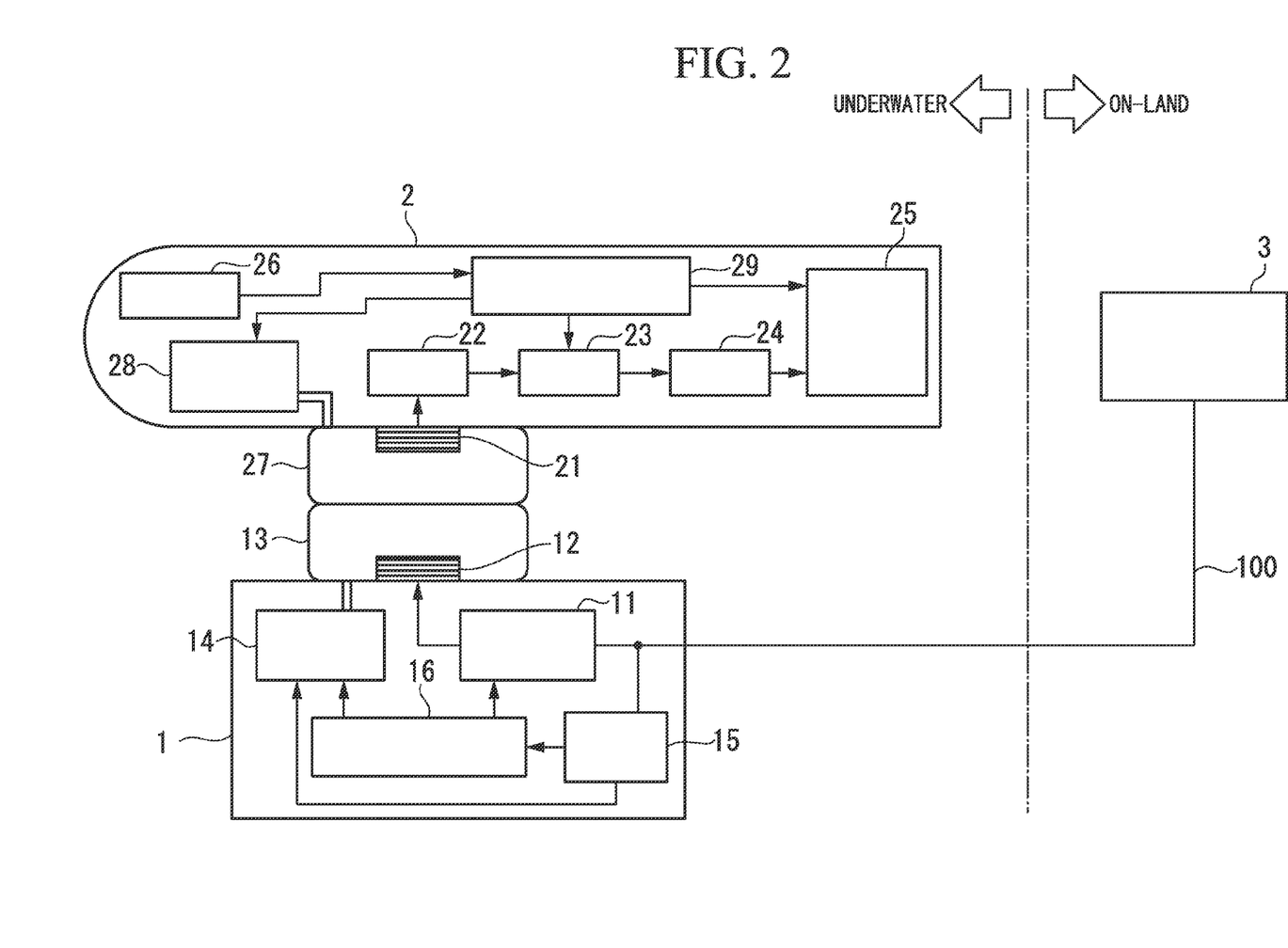
FIG. 2 is a view showing a state in which a power reception balloon of an autonomous underwater vehicle and a power transmission balloon of an underwater base station are inflated during the charging of a battery.

As a result of this, as is shown in FIG. 2, the power reception balloon 27 of the autonomous underwater vehicle 2 and the power transmission balloon 13 of the underwater base station 1 are placed in contact with each other underwater. In this state, the base station control unit 16 of the underwater base station 1 controls the AC/AC converter 11 so as to cause AC power having a predetermined voltage and predetermined frequency that are suitable for transmitting power by means of magnetic field resonance to be output to the power transmission resonance coil 12.

As a consequence, magnetic field resonance occurs between the power transmission resonance coil 12 of the underwater base station 1 and the power reception resonance coil 21 of the autonomous underwater vehicle 2. When this magnetic field resonance occurs, the AC power output from the AC/AC converter 11 is converted into magnetic energy by the power transmission resonance coil 12, and this magnetic energy is then transmitted wirelessly to the power reception resonance coil 21. The magnetic energy is then reconverted into AC power by the power reception resonance coil 21. The AC power that is received by the power reception resonance coil 21 is then converted into DC power by the rectifier circuit 22, which is located at a subsequent stage, and this DC power is then input into the charging circuit 23.

The autonomous vehicle control unit 29 of the autonomous underwater vehicle 2 appropriately charges the battery 24 by controlling the charging circuit 23 while, at the same time, monitoring the state of charge of the battery 24. When the autonomous vehicle control unit 29 has detected that the battery 24 has reached a fully charged state, it switches to the above-described normal mode. The autonomous vehicle control unit 29 controls the power reception balloon control mechanism 28 such that the power reception balloon 27 is fully deflated, and also controls the propulsion/steering mechanism 25 such that the autonomous underwater vehicle 2 collects water quality data while traveling along a prescribed route.

When the base station control unit 16 of the underwater base station 1 detects from a position sensor (not shown) such as a sound wave sensor or optical sensor or the like that the autonomous underwater vehicle 2 has moved, it stops its controlling of the AC/AC converter 11, and, at the same time, controls the power transmission balloon control mechanism 14 such that the power transmission balloon 13 is completely deflated.

As is described above, in the present embodiment, a magnetic field resonance system is employed to transmit power underwater between the underwater base station 1 and the autonomous underwater vehicle 2. Compared to an electromagnetic induction system, this magnetic field resonance system is more resistant to any positional shifting between the power transmission resonance coil 12 and the power reception resonance coil 21 (i.e., has a greater tolerance of any changes in their relative positions), and is able to transmit power using a weaker magnetic field and more efficiently and over a greater distance.

Accordingly, according to the present embodiment, a highly accurate positioning mechanism as is used in the conventional technology which employs electromagnetic induction is not required (in other words, a commonplace position sensor such as the aforementioned sound wave sensor or optical sensor or the like is sufficient). As a result of this, it is possible for power to be transmitted underwater between the underwater base station 1 and the autonomous underwater vehicle 2 at a low cost.

Moreover, in the present embodiment, the power transmission resonance coil 12 is covered by the power transmission balloon 13, and the power reception resonance coil 21 is covered by the power reception balloon 27. As a result of this, it is possible to prevent the magnetic field being disturbed by the effects of ions and the like contained in the seawater, and it is thereby possible to prevent the efficiency of the power transmission between the power transmission resonance coil 12 and the power reception resonance coil 21 (i.e., between the underwater base station 1 and the autonomous underwater vehicle 2) from deteriorating.

Note that the present invention is not limited to the above-described embodiment, and variant examples such as those described below are also possible.

(1) In the above-described embodiment, in order to extract the water quality data saved in the autonomous underwater vehicle 2 to the outside, it is necessary to recover the autonomous underwater vehicle 2 to a surface vessel or the like. In contrast to this, as is shown, for example, in FIG. 3, it is possible to employ a system structure in which the underwater base station 1 is connected by means of a communication cable 200 to an on-land water quality data control device 4, and during a power transmission (i.e., when the battery 24 is being charged) the autonomous underwater vehicle 2 transmits water quality data wirelessly via an antenna 30 to the underwater base station 1, and the underwater base station 1 transmits the water quality data received via the antenna 17 from the autonomous underwater vehicle 2 to the water quality data control device 4 by means of a cable.

Figure 3:
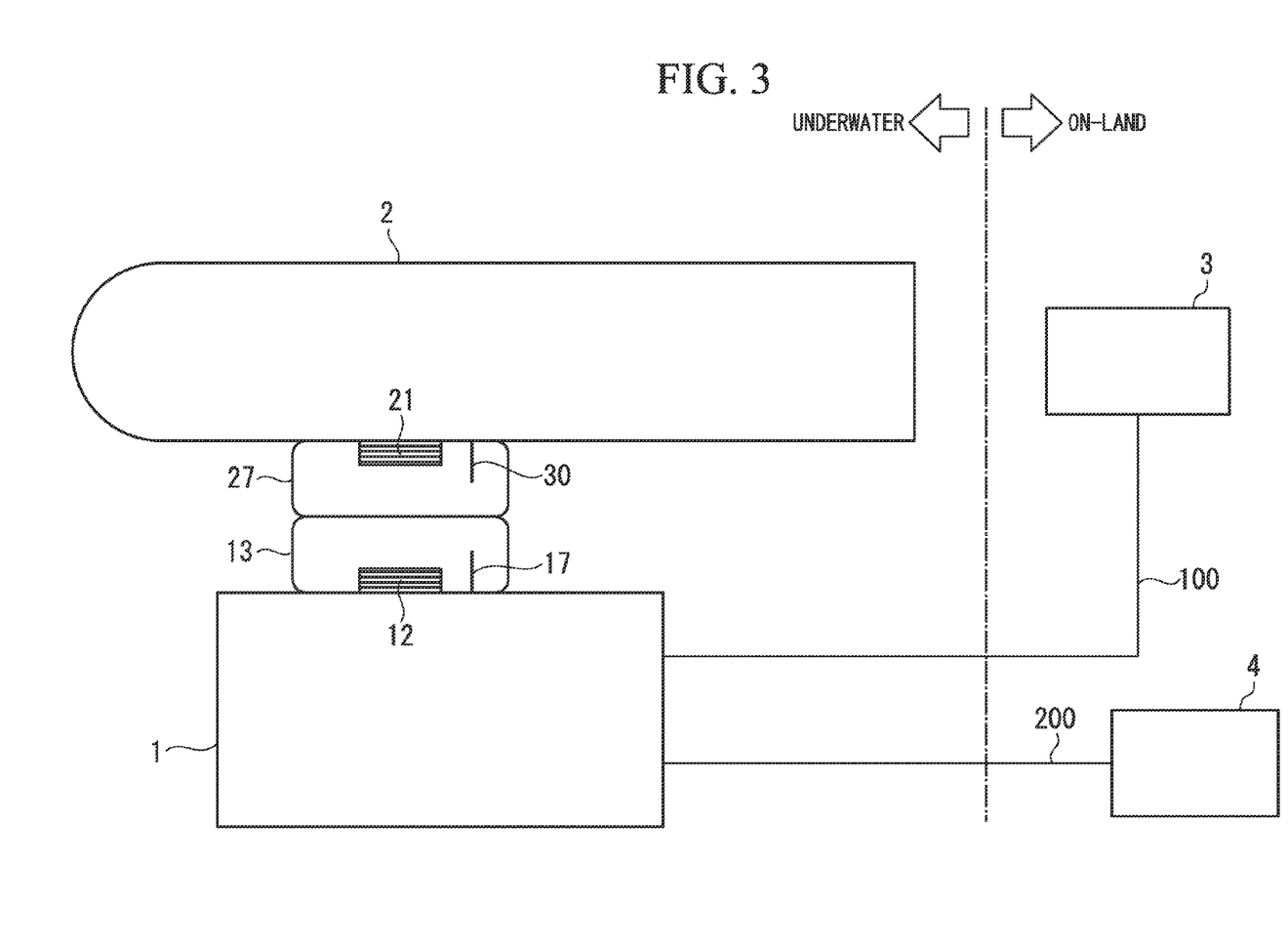
FIG. 3 is a first explanatory view relating to a variant example of the present embodiment.

In the system structure shown in FIG. 3, it is assumed that water quality data is communicated wirelessly via radio waves. Because of this, it is necessary for the antenna 30 to be covered by the power reception balloon 27 and for the antenna 17 to be covered by the power transmission balloon 13. However, if sound wave communication, optical communication, or infrared communication or the like is used for the wireless communication of the water quality data, then it is not necessary to provide the antennas 17 and 30.

Figure 4A:
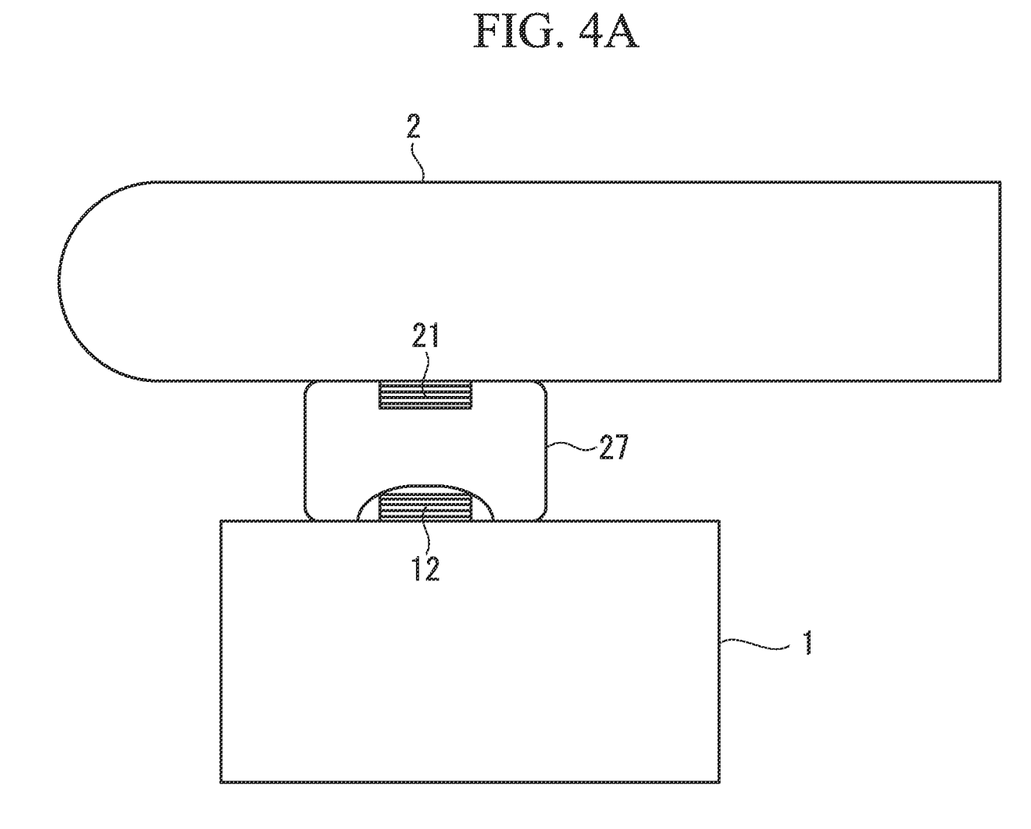
FIG. 4A is a second explanatory view relating to a variant example of the present embodiment.
Figure 4B:
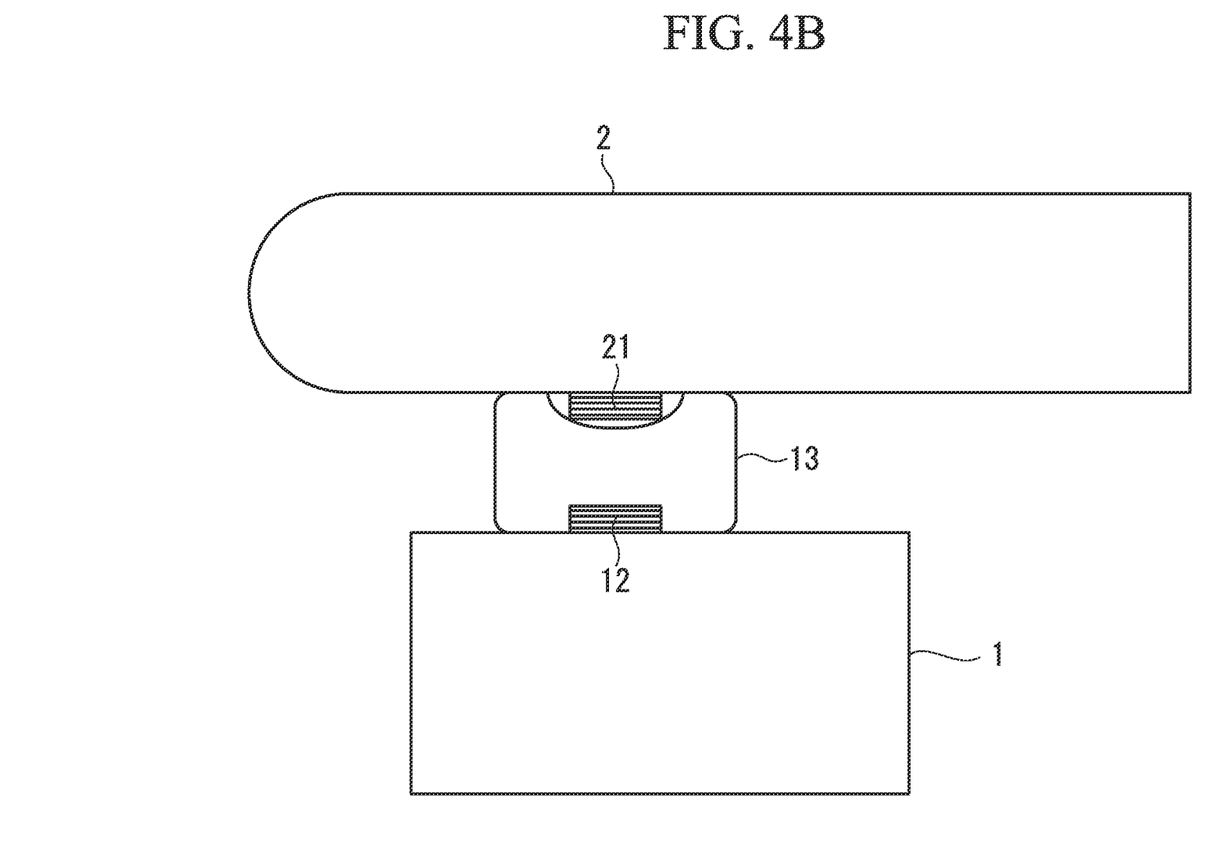
FIG. 4B is a third explanatory view relating to a variant example of the present embodiment.

(2) In the above-described embodiment, a case is described in which balloons (i.e., the power transmission balloon 13 and the power reception balloon 27) that internally contain resonance coils (i.e., the power transmission resonance coil 12 and the power reception resonance coil 21) are provided in both the underwater base station 1 and the autonomous underwater vehicle 2. However, the present invention is not limited to this and it is also possible to provide a balloon that internally houses a resonance coil in only one of the underwater base station 1 and the autonomous underwater vehicle 2. FIG. 4A shows an example of a case in which the power reception balloon 27 that internally contains the power reception resonance coil 21 is only provided in the autonomous underwater vehicle 2. FIG. 4B shows an example of a case in which the power transmission balloon 13 that internally contains the power transmission resonance coil 12 is only provided in the underwater base station 1. It is also possible to provide a plurality of power transmission coils, or to separately prepare those balloons having no power transmission function, arranged side-by-side in parallel to the autonomous underwater vehicle, which will prevent the autonomous underwater vehicle 2 being damaged by direct contact with the underwater base station 1 or with a jetty.

In the above description, the power transmission resonance coil 12 and the power reception resonance coil 21 both have protruding structures, however, it is also possible to employ a structure in which these are built into the underwater base station 1 and the autonomous underwater vehicle 2 respectively, and an aperture portion is provided in each one that emits electromagnetic waves to the outside and is covered by the power transmission balloon 13 and the power reception balloon 27 respectively.

In this case, when the power reception balloon 27 is being inflated, it is possible to utilize a 'jamming transition' phenomenon in order to cover the power transmission resonance coil 12 and fix it in position by means of the power reception balloon 27. Namely, the power reception balloon 27 is filled in advance with a powder or granulated material. After the power reception balloon 27 has been inflated such that it covers the power transmission resonance coil 12, then the gas inside the power reception balloon 27 is suctioned out. As a result of this, the interior of the balloon is fixed in place by the friction of the powder or granulated material, and it is possible to firmly fix the power transmission resonance coil 12 in position by means of the power reception balloon 27. Conversely, when the power transmission balloon 13 is being inflated, it is possible to use the 'jamming transition' phenomenon in order to cover the power supply resonance coil 21 and fix it in position by means of the power transmission balloon 13. Namely, the power reception balloon 13 is filled in advance with a powder or granulated material. After the power reception balloon 13 has been inflated such that it covers the power transmission resonance coil 21, the gas inside the power reception balloon 13 is suctioned out. As a result of this, the interior of the balloon is fixed in place by the friction of the powder or granulated material, and it is possible to firmly fix the power reception resonance coil 21 in place by means of the power transmission balloon 13. Note that the powder or granulated material may be formed from a material having a high level of magnetic permeability, or from a ceramic material that does not obstruct the wireless supply of power (for example, alumina, mullite, ferrite, forsterite, zirconia, zircon, cordierite, aluminum nitride, silicon nitride, silicon carbide, lead zirconate titanate, and conjugated compounds of these), and compounds of these with resins containing a high polymer material.

If a structure is employed in which the power transmission resonance coil 12 and the power reception coil 21 are built into the underwater base station 1 and the autonomous underwater vehicle 2 respectively, and an aperture portion is provided in each one that emits electromagnetic waves to the outside and is covered by the power transmission balloon 13 and the power reception balloon 27 respectively, then it is possible to introduce the powder or granulated material at the same time as the gas or fluid is introduced into the interior of each balloon such that the balloon portions become intertwined with each other, and to then discharge only the gas or fluid at mutually offset times in each balloon.

(3) In the above-described embodiment, a case is described in which the power-transmitting device (i.e., the underwater base station 1) is fixed underwater, and the power-receiving device (i.e., the autonomous underwater vehicle 2) is able to move through the water. However, the present invention is not limited to this and it is also possible for this relationship to be reversed. Alternatively, it is also possible to employ a system structure in which both the power-transmitting device and the power-receiving device are able to move freely through the water. The present invention is also not limited to sea water, and can also be applied broadly to the transmission of power in any water such as lakes, rivers, and swamps and the like.

(4) The power transmission resonance coil 12 and the power reception resonance coil 21 are not limited to being helical coils. Provided that the transmission of power is possible wirelessly by means of magnetic field resonance between the power transmission resonance coil 12 and the power reception resonance coil 21, then a coil of any desired shape and configuration such as solenoid or the like may be used. Moreover, the shape, configuration, and size of the two coils does not need to be the same.

INDUSTRIAL APPLICABILITY

According to the power transmission system of the present invention, it is possible to achieve underwater power transmissions at low cost between a power-transmitting device and a power-receiving device. Moreover, it is possible to prevent the magnetic field being disturbed by the effects of ions and the like contained in the water, and it is thereby possible to prevent the efficiency of the power transmission between the power-transmitting device and the power-receiving device from deteriorating.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

DESCRIPTION OF REFERENCE SIGNS

A . . . Power transmission system, 1 . . . Underwater base station (Power-transmitting device), 12 . . . Power transmission resonance coil, 13 . . . Power transmission balloon, 14 . . . Power transmission balloon control mechanism, 2 . . . Autonomous underwater vehicle (Power-receiving device), 21 . . . Power reception resonance coil, 24 . . . Battery, 27 . . . Power reception balloon, 28 . . . Power reception balloon control mechanism, 3 . . . Electrical power system

The invention claimed is:

1. A power transmission system that transmits power underwater between a power-transmitting device and a power-receiving device of which at least one is capable of moving freely underwater, wherein
    the power-transmitting device and the power-receiving device are each provided with a resonance coil that performs the power transmission wirelessly underwater by means of magnetic field resonance, and
    at least one of the power-transmitting device and the power-receiving device is provided with a balloon that internally houses the resonance coil of its own device.

2. The power transmission system according to claim 1, wherein at least one of the power-transmitting device and the power-receiving device is provided with a balloon control mechanism that, during a power transmission, causes the balloon to inflate, and at other times, causes the balloon to be deflated.

3. The power transmission system according to claim 1, wherein
    the power-receiving device is an autonomous underwater vehicle that collects water quality data as it moves through the water under battery power, and
    the power-transmitting device is an underwater base station that is installed in a predetermined location underwater and is connected by a cable to an on-land electrical power system, and receives from the electrical power system a supply of power that is to be transmitted to the autonomous underwater vehicle.

4. The power transmission system according to claim 2, wherein
    the power-receiving device is an autonomous underwater vehicle that collects water quality data as it moves through the water under battery power, and
    the power-transmitting device is an underwater base station that is installed in a predetermined location underwater and is connected by a cable to an on-land electrical power system, and receives from the electrical power system a supply of power that is to be transmitted to the autonomous underwater vehicle.

5. The power transmission system according to claim 3, wherein
    the autonomous underwater vehicle wirelessly transmits the water quality data to the underwater base station during a power transmission, and
    the underwater base station is connected by cable to an on-land water quality data control device, and transmits the water quality data that it receives from the autonomous underwater vehicle by cable to the water quality data control device.

6. The power transmission system according to claim 4, wherein
    the autonomous underwater vehicle wirelessly transmits the water quality data to the underwater base station during a power transmission, and
    the underwater base station is connected by cable to an on-land water quality data control device, and transmits the water quality data that it receives from the autonomous underwater vehicle by cable to the water quality data control device.

* * * * *